United States Patent [19]
Schoess et al.

[11] Patent Number: 5,549,803
[45] Date of Patent: Aug. 27, 1996

[54] SMART FASTENER

[75] Inventors: Jeffrey N. Schoess, Buffalo; Gary D. Havey, Maple Grove, both of Minn.

[73] Assignee: Honeywell Inc., Minneapolis, Minn.

[21] Appl. No.: 182,903

[22] Filed: Jan. 14, 1994

[51] Int. Cl.⁶ .................................................. G01N 27/26
[52] U.S. Cl. ............................ 204/404; 204/400; 411/14
[58] Field of Search .......................... 204/153.1, 153.11, 204/404, 400; 411/14

[56] References Cited

U.S. PATENT DOCUMENTS

| | | | |
|---|---|---|---|
| Re. 30,183 | 1/1980 | Popenoe | 411/14 |
| 2,947,679 | 8/1960 | Schaschl et al. | 204/404 |
| 3,491,012 | 1/1970 | Winslow | 204/404 |
| 4,133,732 | 1/1979 | Boeke | 204/419 |
| 4,295,377 | 10/1981 | Couchman | 73/761 |
| 4,380,763 | 4/1983 | Peart et al. | 340/870 |
| 4,425,193 | 1/1984 | Taylor | 204/404 |
| 4,553,124 | 11/1985 | Malicki | 411/14 |
| 5,222,849 | 6/1993 | Walton | 411/14 |
| 5,243,298 | 9/1993 | Runner | 204/404 |
| 5,286,357 | 2/1994 | Smart et al. | 204/404 |
| 5,306,414 | 4/1994 | Glass et al. | 204/404 |
| 5,310,470 | 5/1994 | Agarwala et al. | 204/404 |

FOREIGN PATENT DOCUMENTS

| | | |
|---|---|---|
| 1049911A | 3/1991 | China . |
| 0100814A1 | 2/1984 | European Pat. Off. . |
| 0518508A1 | 12/1992 | European Pat. Off. . |
| 0528554A2 | 2/1993 | European Pat. Off. . |
| 62-130320A | 6/1987 | Japan . |
| 3269234 | 11/1991 | Japan ................ 411/14 |
| 2212284 | 7/1989 | United Kingdom ........... 411/14 |
| 2231163 | 11/1990 | United Kingdom ........... 411/14 |

OTHER PUBLICATIONS

J. Gerardi et al., "Health monitoring system for aircraft", *Active Materials and Adaptive Structures*, Proceedings of ADPA/AIAA/ASME/SPIE Conf., Nov. 4–8, 1991, on pp. 403–406.

P. S. Rutherford et al., "Aircraft structural integrity and 'smart' structural health monitoring", *Active Materials and Adaptive Structures*, Proceedings of ADPA/AIAA/ASME/SPIE Conf., Nov. 4–8, 1991.

*Primary Examiner*—T. Tung
*Attorney, Agent, or Firm*—John G. Shudy, Jr.

[57] ABSTRACT

A smart fastener having corrosion detection features. Within the fastener is a corrosion detecting array that receives an electrolyte that corrodes sacrificial materials formed on electrodes of the corrosion detecting array. The materials are the same as those materials which are secured, fastened, or attached by the fastener. There is parallel corrosion of the sacrificial materials and the attached materials since the electrolyte which is channeled via capillary tubes into the corrosion detecting array is the same electrolyte that is in the environment of the fastened materials. Other electrodes sense various properties of the electrolyte. Information sensed by the corrosion sensing electrodes of the array is in the form of very small electrical signals which are amplified and stored in an analog storage memory. A clock and addressing device time stamps and address the signals. An interface circuit enables a user to electronically access corrosion and related signals without removing or in any way dismantling the fastener.

20 Claims, 9 Drawing Sheets

SMART FASTENER

BACKGROUND OF THE INVENTION

The invention pertains to corrosion to detection and particularly detection of metal corrosion in aircraft structure joints. More particularly, the invention pertains to sensors of metal corrosion in aircraft structure joints.

The applicants have recently devoted significant research efforts to understand the effects of corrosion in commercial transport and military aircraft. They have learned that non-destructive inspection of aircraft for corrosion involves an additional dimension of complexity beyond conventional non-destructive evaluation (NDE) inspection techniques for structural integrity problems such as fatigue cracking. Fatigue crack inspection is typically localized to joints and high stress locations on the fuselage structure. Hidden corrosion effects can occur, not only at such locations but throughout the aircraft structure. FIG. 1 shows some of the types of corrosion that occur on aircraft. Corrosions 11, 12, 13, 14, 15 and 16 are examples of pitting, inter granular exfoliation, stress corrosion cracking, inter granular cracking, crevice and galvanic corrosion and uniform microbial corrosion, respectively.

Corrosion occurs in areas of the fuselage subject to excess moisture or wetted by other fluids. These areas include the bilge of the fuselage for transport aircraft around wing fastener holes (primarily exfoliation), fuel shelf areas, wheel well shelves/backwalls in various aircraft, all doors including cargo access and landing gear doors.

Several existing non-destructive inspection (NDI) methods are available to detect corrosion, but each method is optimized to detect a particular type of corrosion. these detection methods include visual, tap test, electrical resistance probing, electrochemical analysis, ultrasonic, eddy current, X-ray radiography, and acoustic emission with heat. Visual inspection is appropriate for checking surface conditions such as pitting or exfoliation (blistering) but does little to detect hidden corrosion between lap joints. Acoustic emission NDE (e.g., the acoustic detection of hydrogen bubbles or gas) can detect material loss gaps between lap joints and structural cracks that could cause loss of structural integrity, but does not directly quantify the percentage of material loss or corrosion products.

The present invention makes it possible to detect hidden corrosion effects in aircraft structures. A key technical requirement is the detection of corrosion within the aircraft structure just below the head of an aircraft fastener, between lap joints or on the aircraft fuselage inner wall. The smart fastener concept focuses on the novel idea of integrating an electrochemical-based sensor directly into the aircraft structure to measure the evidence of active corrosion as an in-situ measurement without reducing aircraft structural integrity.

SUMMARY OF THE INVENTION

The present invention is an "in-situ" measurement approach which makes it possible to detect hidden corrosion in aircraft structures. It is composed of a standard aircraft HI-LOK fastener which has been modified to embody a corrosion sensing element and placed into a lap joint(or bulkhead) assembly of an aircraft. This sensor contains a multielement micro electrode array detector that measures the concentration of corrosion ions in a solution and smart electronics module to convert the corrosion data into a readout display or record information for future retrieval and aircraft structural maintenance support.

The invention provides in-situ corrosion detection. The fastener system measures the effect of hidden corrosion directly within the structure of interest as an 'in-situ' electrochemical measurement. Conventional NDI techniques such as image processing (IR or visible light based), resistance probes, eddy current, acoustic emission (AE) and X-ray methods can detect surface (i.e., surface cracks caused by corrosion) buildup or material loss. However, none of these alternate methods can reliably detect hidden and inaccessible corrosion at a lap joint interface, a bulkhead to wing attachment interface, or under a wing fairing.

Another feature is corrosion growth tracking. Fastener performs autonomous long-term data logging which facilitates tracking the corrosion process within the aircraft structure and storing historical results within a non-volatile analog memory element. To the applicants' knowledge, this capability has not been duplicated anywhere else.

Still another feature is corrosion prediction. Each array element in the micro electrode sensor measures the presence of specific corrosion-related ions. The time-based trend signature based on the individual's element potential may prove to be a useful method for predicting corrosion behavior.

The fastener design embodies the measurement of corrosion within a standard aircraft HI-LOC fastener without loss of aircraft structural integrity. This new packaging technique holds much potential for incorporating other types of sensing (i.e., acoustic emission and airflow) and structural control elements (i.e., airflow deflection and vibration suppression). To the applicants' knowledge, this method has not been duplicated in the related art.

DESCRIPTION OF THE SPECIFIC EMBODIMENT

Figure 1A:
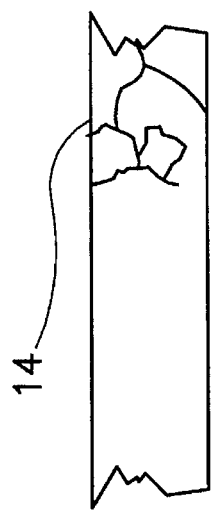
FIG. 1 shows examples of corrosions.
Figure 1B:
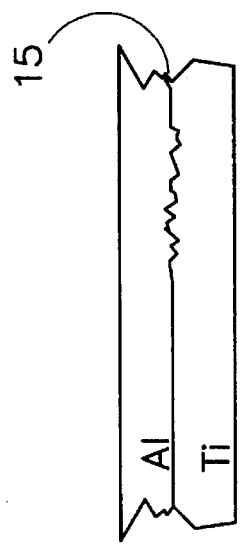
Figure 1C:
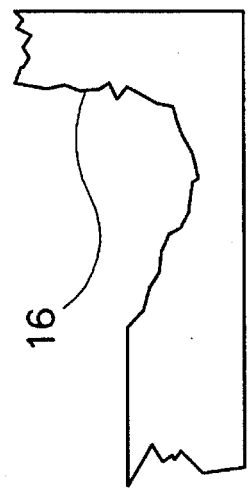
Figure 1D:
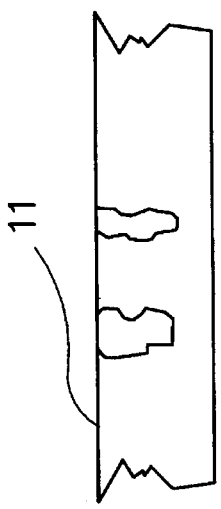
Figure 1E:
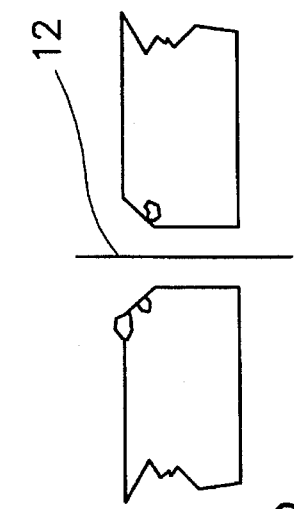
Figure 1F:
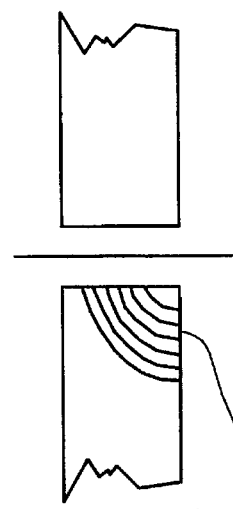
Figure 2:
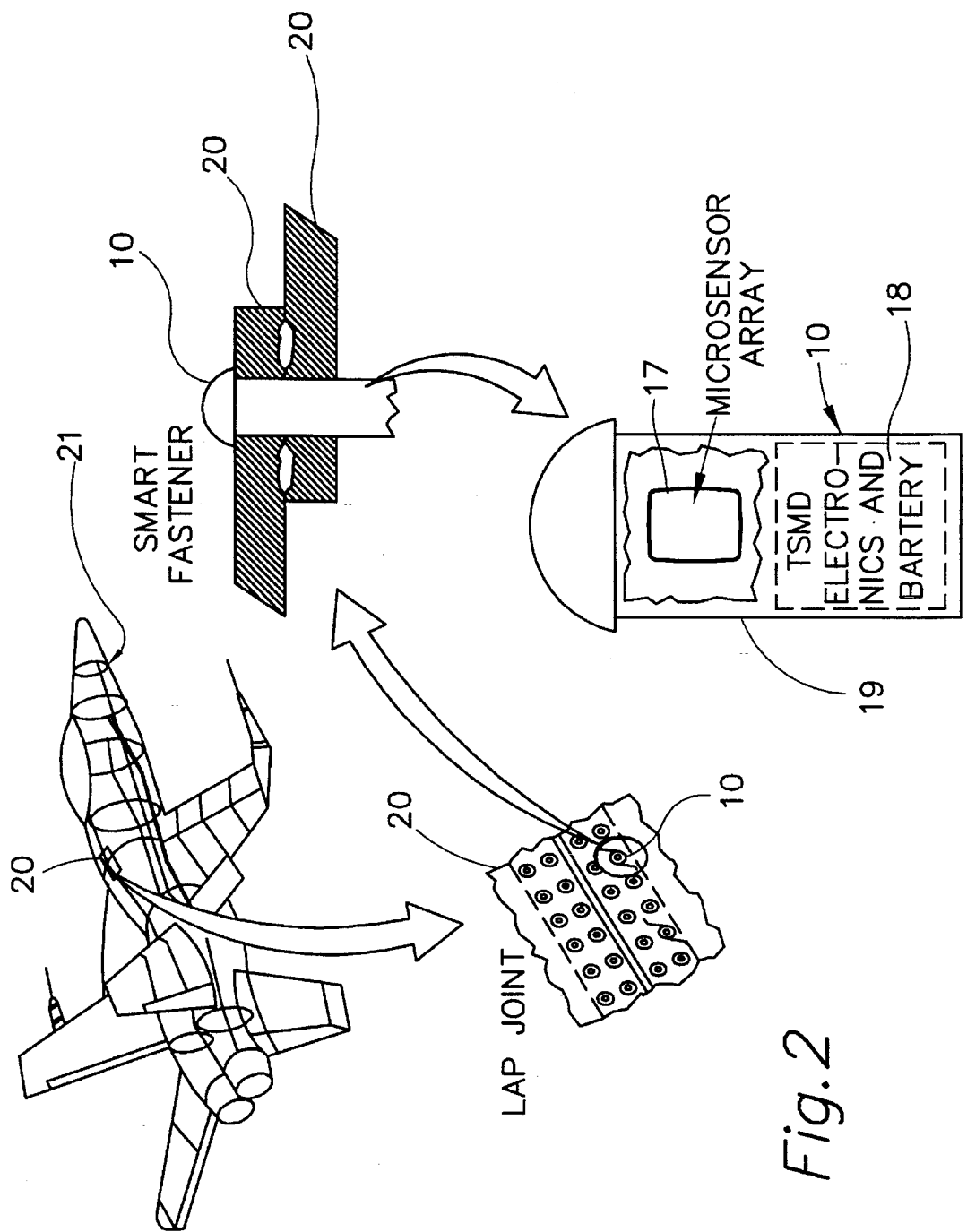
FIG. 2 shows the fastener and its relationship to an application.
Figure 3A:
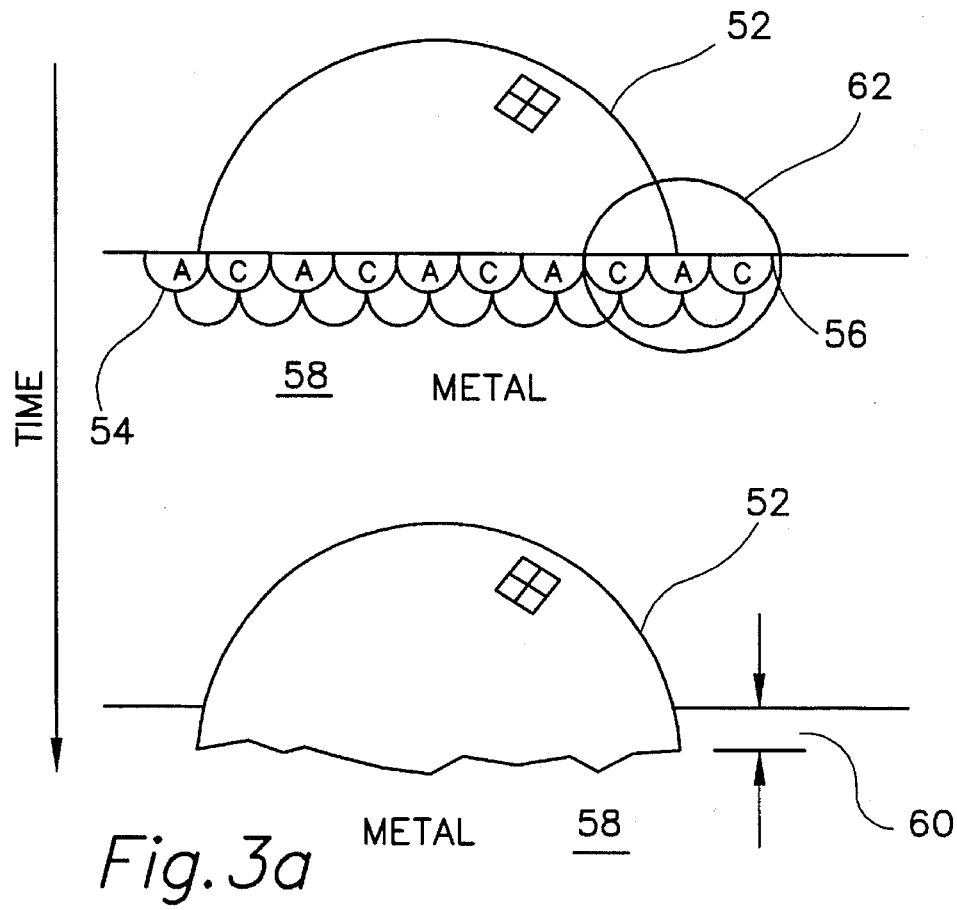
FIGS. 3a and 3b illustrate the electrical aspect of corrosion.
Figure 3B:
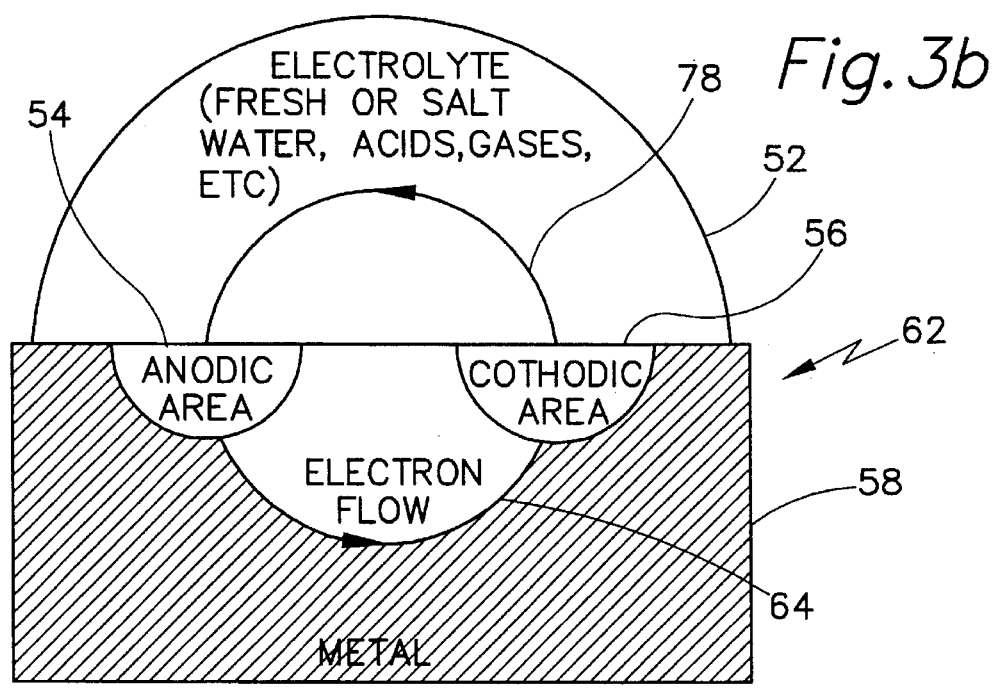

The overall smart fastener 10 system is illustrated in FIG. 2 which highlights a smart aircraft fastener 10 which is constructed to detect aircraft 21 corrosion as an in-situ electrochemical measurement process. System 10 incorporates embedding a sensing element 17 and electronics 18 into an aircraft fastener body 19 which has dual-use applicability to detect structural integrity related to metal 20 fatigue and cracking with the incorporation of a broad band acoustic emission transducer. The aging aircraft program would relate acoustic emission events with the release of hydrogen gas in a corrosion reaction process of an aging aircraft structure. FIGS. 3a and 3b illustrates the corrosion process discussed below.

Figure 4:
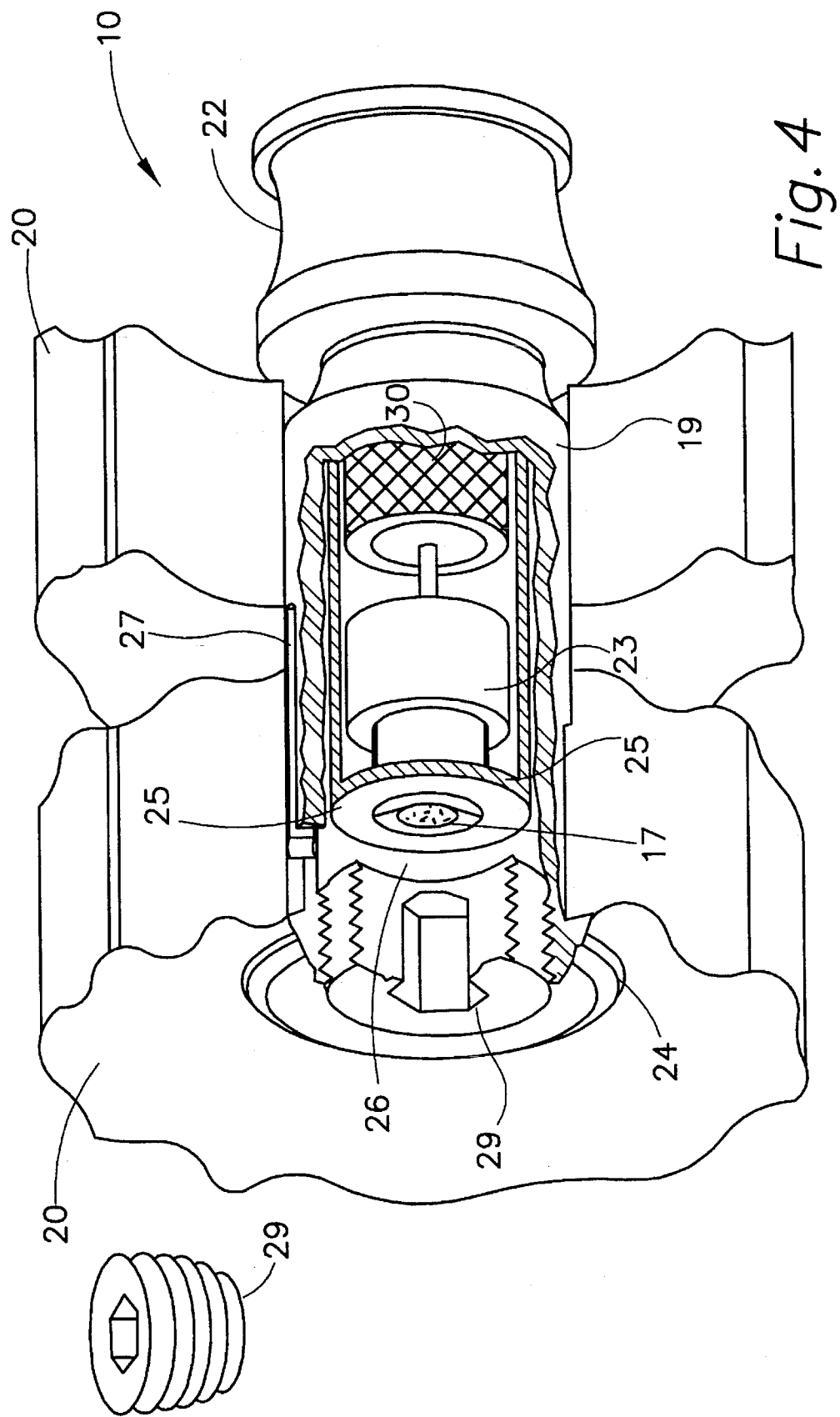
FIG. 4 is a cut-away view of the fastener.

FIG. 4 is a cut-away view of smart fastener 10 which is a 0.5 inch diameter protruding-head fastener (HL6201 or equivalent) inserted in lap joint assembly 20 retained with a torque-sensitive nut 22 which may be a HI-LOC fastener which is designed to snap off at the application of a certain amount of torque, such as with an allen wrench in a slot recessed in nut 22. The fastener body 19 material consists of a high-strength corrosion resistant steel (Series 300) with 0.050 thick walls. Smart fastener electronics 23 are shown located within fastener body 19 in a hermetically sealed package. Sensor array 17 and environmental cavity 26 are sealed from electronics 18 by ceramic substrate 25. Access to electronics 18 may be attained by removal of screw 29 with the aid of an allen wrench or other slot type tool.

FIG. 3a illustrates the principle of a corrosion that the subject invention is designed to detect and measure. Electrolyte 52 which may be fresh or salt water, an acid, gas or other like substance, provides a corrosive environment. Tiny anodes 54 and cathodes 56 form on the surface of metal 58. With the passage of time, anodes 54 and cathodes 56 polarize to the corrosion potential, constantly switching their nature, thereby causing uniform surface corrosion 60. FIG. 3b shows a closer view 62 of the corrosion activity having an electron flow 64 and an ion flow 78.

Figure 9:
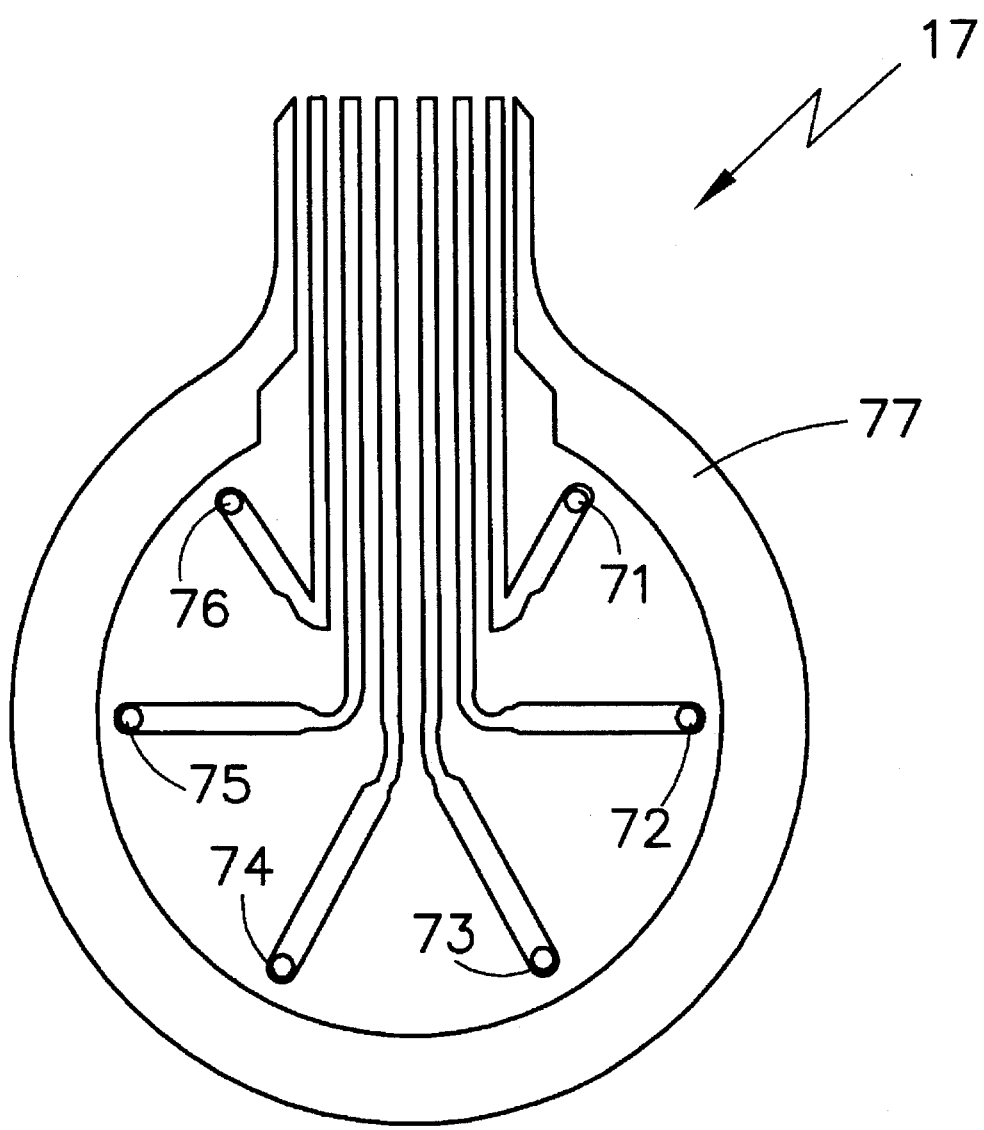
FIG. 9 is a layout of the multielement corrosion microsensor.

A multielement electrochemical sensor mounted on a two-sided ceramic substrate 25 and located with an integral corrosion-sensing environmental chamber at a head 24 of fastener 10. The multielement array 17 is electrically connected to sensor electronics 23 module via glass ferrule feed-through connection in ceramic substrate 25. The fastener 10 principle of operation for detecting corrosion is as follows: a corrosive electrolyte 52 in the ambient environment of fastener 10 (i.e., $H_2O$) seeps into environmental chamber 26 via the multiple 0.010 inch electrolyte capillary tubes 27 located radially in the wall of the fastener body 19. Each individual capillary tube 27 has a designated length depending on the desired location of sensing location of corrosion, either towards the head 24 of fastener 10, between lap joint 20 to detect corrosive agents that enter at unsealed skin edges or along inner fuselage wall 20 of the aircraft 21. Electrolyte 52, which contains corrosive ions of interest, goes up along fastener wall 19 due to the tube 27 capillary effect and into fastener environmental chamber 26. The electrochemical sensor then detects the unique electrochemical properties of the electrolyte which are then be sampled, recorded and stored in the analog memory 41 for detailed analysis and data retrieval by aircraft maintenance personnel. A sensing element 75, for instance, contains microscopic regions of anodes 54 and cathodes 56 which create a "localized" corrosion cell generating an ionic current flow 78 as shown in FIGS. 3b and 9. Reference electrode 77 senses the potential difference between itself due to localized corrosion reaction and micro array element, with the reference electrode 77 in thermometric equilibrium. An input impedance of 10 to the 12th power must be maintained at the micro array element electrical input. Microsensor array 17 detects reactions occurring at the sensor (electrode) surface. Often, the sensing surface 25 is metallic, but can be glass, ceramic, or a polymer layer covering a metal, or a chemical coating on a metal. Microsensor 17 is typically immersed in the environment to be tested, usually water. The chemical compounds or ions to be detected are dissolved in the water in contact with the sensor surface. The sensing reaction usually involves the addition or removal of an electron from the compound of interest. For potentiometric type measurements, a unique potential develops between the reference electrode and sensing element due to ionic interaction. A typical electrode design is an ion-selective electrode, where Cl+ is implanted into a silver substrate to produce a Cl− ion-selective electrode. $IrO2$ (anodically oxidized iridium) is typically sputtered on a silicon substrate to create a pH sensitive microsensor element 73.

Figure 5:
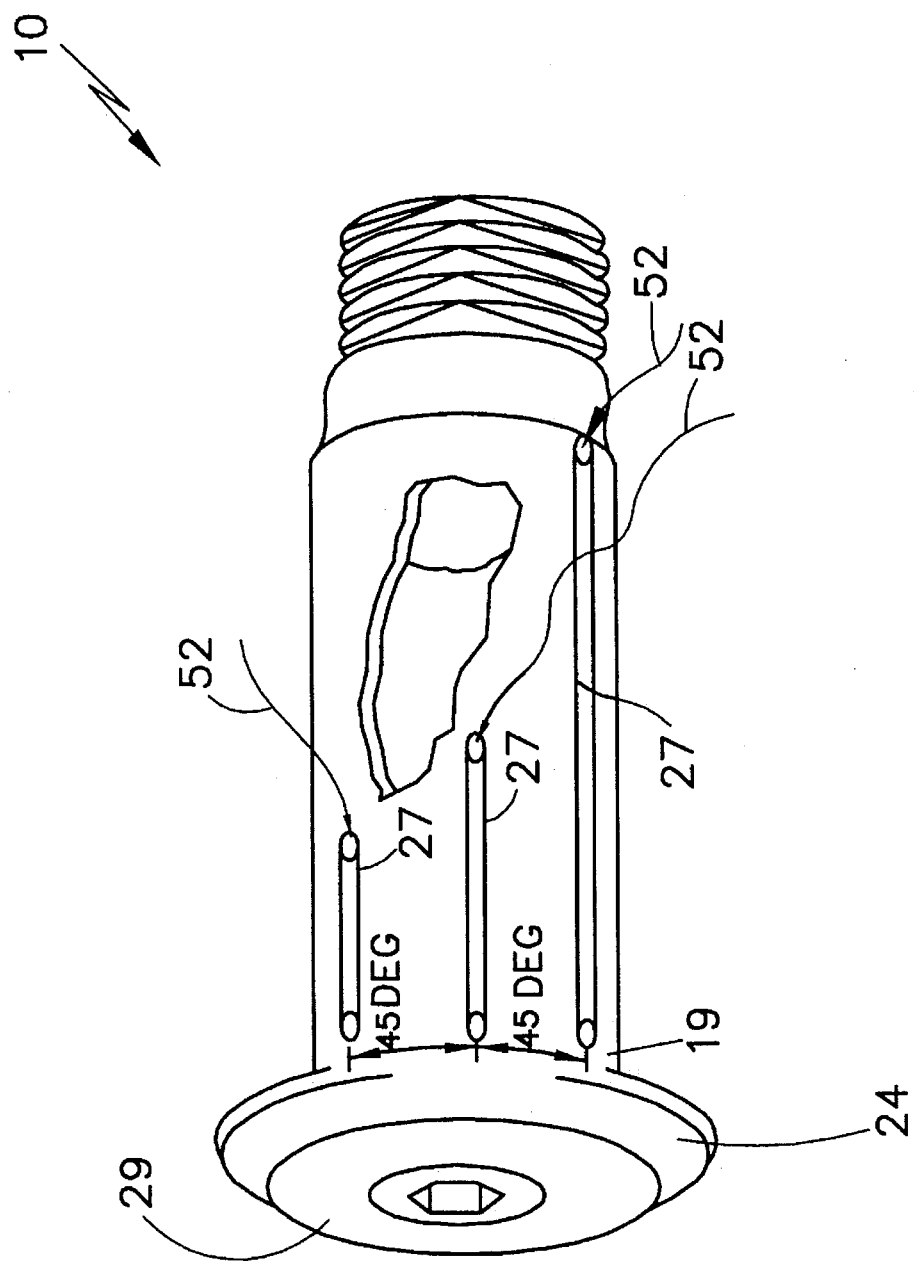
FIG. 5 shows the body of the fastener.

FIG. 5 illustrates fastener 10, absent nut 22, with electrolyte 52 and capillary tubes 27 of different lengths and radial spacing of 45 degrees. Various fastener 10 designs can be manufactured to measure corrosion effects at specific locations along the fastener shank 19 if desired. The significant advantages of this packaging design approach include complete compatibility with existing aircraft fastener maintenance procedures, no loss of aircraft structural integrity due to insertion, ease of repair and replacement of electronics, excellent selectivity of corrosion measurement via capillary tube 27 length, and excellent potential for low-cost fabrication.

A mechanical design analysis of fastener 10 has been performed. Aircraft torque specifications require that fastener 10 be able to sustain up to approximately 50 ft-lbs of longitudinal torque. A fastener having a hole in the center has a lower tensile strength than the solid counterpart. The maximum tensile load supported by a hollow fastener can be calculated approximately using the equation:

$$P_T = (A_T - A_H) \cdot T_s,$$

where:

$P_T$=tensile load (lb.), $A_T$=tension area (sq. in.), $A_H$=hole area (sq. in.), and $T_s$=tensile strength(psi).

A feature of fastener 10 is a dry seal access screw or plug 29 as shown in FIG. 4. Plug 29 is a commercially available stainless steel $\frac{1}{16}$ NPT dry seal plug to facilitate removal and refurbishment of electronics module 23 without removing fastener 10 from the aircraft 21 structure. A hex key slot is located at the center of plug 29 to facilitate electronics removal. This type of maintenance activity can be performed if the multielement electrochemical sensor has been contaminated or the electronics battery 30 requires replacement. The tensile load resulting from the applied torque must not exceed the maximum limit. The selection of a high-strength steel (i.e., AISI 4340 or equivalent) may be necessary to compensate for the degradation of strength due to the presence of a hole in fastener body 19. Various materials may be used to fabricate fastener 10, such as cadmium plated ferrous steel, stainless steel or titanium. The fastener 10 structure itself should not be susceptible to corrosion.

Figure 6:
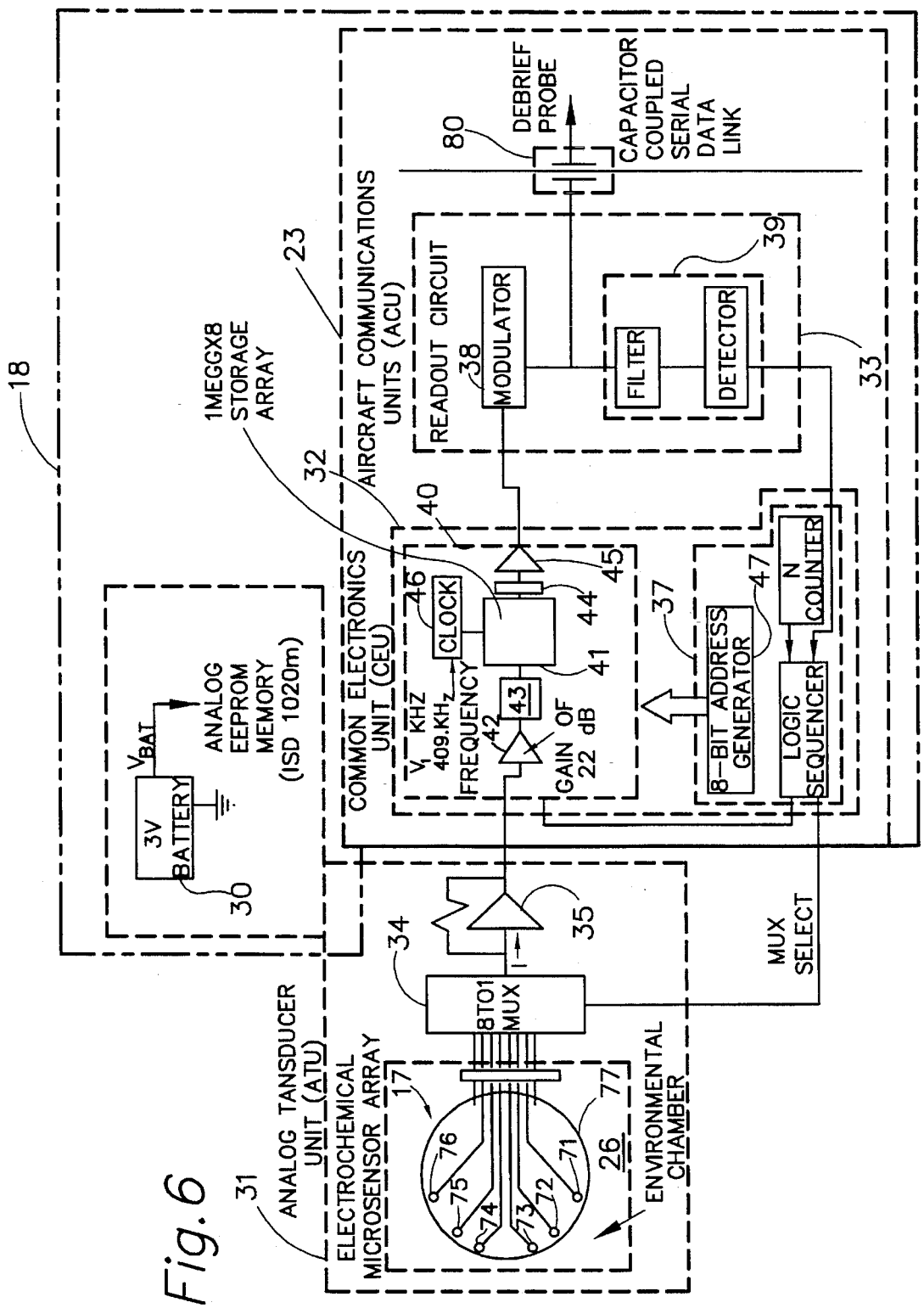
FIG. 6 is a diagram of the electronics.
Figure 7:
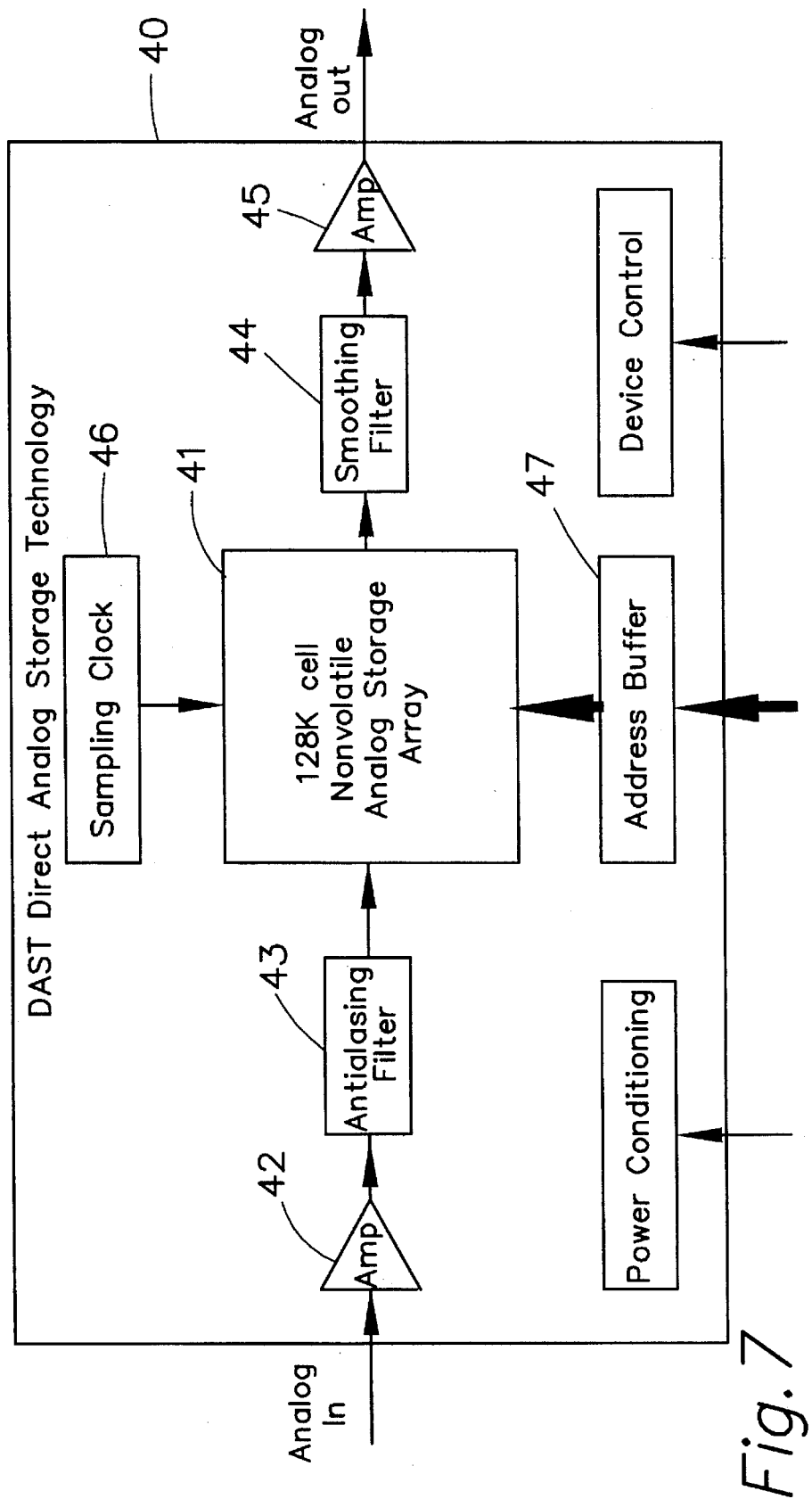
FIG. 7 is a block diagram of the direct analog storage memory.

Fastener 10 electronics system as shown in FIG. 6 is functionally partitioned into three modules: analog transducer unit (ATU) 31, common electronics unit (CEU) 32, and aircraft communications unit (ACU) 33. ATU 31 contains electrochemical micro sensor array 17, analog multiplexer 34, and signal amplifier 35. CEU 32 incorporates a "common electronics" digital core including a solid-state analog memory storage device 40, state machine sequence logic 37, and integral rechargeable lithium polymer battery cell 30. ACU 33 contains a low power transmitter 38/receiver 39 circuit to facilitate structural maintenance data retrieval and collection.

Another feature of fastener 10 is direct analog storage technology memory (DASM) 40. The ability to store in-situ structural health monitoring corrosion data in the fastener 10 electronics is essential to record time-related corrosion events and track structural material loss. DASM 40 provides the means to store the corrosion data in analog form directly into and read directly from the DASM storage device 41. DASM 40 is an analog electrically erasable programmable read only memory (EEPROM) device. DASM 40 has an input amplifier 42 with an output connected to an antialiasing filter 43. The output of the antialiasing filter 43 goes to a 128 thousand cell nonvolatile analog storage array 41. The output of array 41 goes to smoothing filter 44. Signals from filter 44 go to output amplifier 45. Also, provided to array 41 are clock signals from sampling clock 46 and address control logic signals from address buffer 47. DASM 40 EEPROM is organized as a low power 128K analog storage array 41 that stores analog data directly without needing a digital format before storage. Generator 47 is state machine which has a binary counter that generates addresses so that records are address and can be pulled from analog array 41 for review. However, when records are pulled, that portion of the memory is cleared for new recordings. If records are not pulled and all of the memory space is occupied, then new data is written over the oldest records. Records are pulled out of ACU 33 through capacitor coupled serial data link 80, without dismantling or removing fastener 10. Alternatively, electronics 18 may be removed and then the records pulled out.

DASM device 40 provides several key advantages over conventional digital memory technology such as higher storage density per unit volume, zero-power storage capability, no analog to digital (A/D) converter support, and a ten year data retention. DASM analog array 41 consists of 128 thousand cells—the equivalent of one Megabit of digital storage or 8:1 improvement over conventional digital data storage. In digital technology, one of two voltage levels (i.e., bit) is stored in each memory cell while DASM technology currently stores one of 230 voltage levels. Since the autonomous operation of fastener 10 requires minimum power consumption and package size constraints due to aircraft fastener form factor limitations, DASM analog array 41 is preferred. DASM 40 features non-volatile EEPROM technology, which requires no power to store structural corrosion data for up to 10 years. The DASM design eliminates the need for digital data converters, modulators, and battery backup circuits which reduces fastener 10 parts count by a factor of two.

Figure 8:
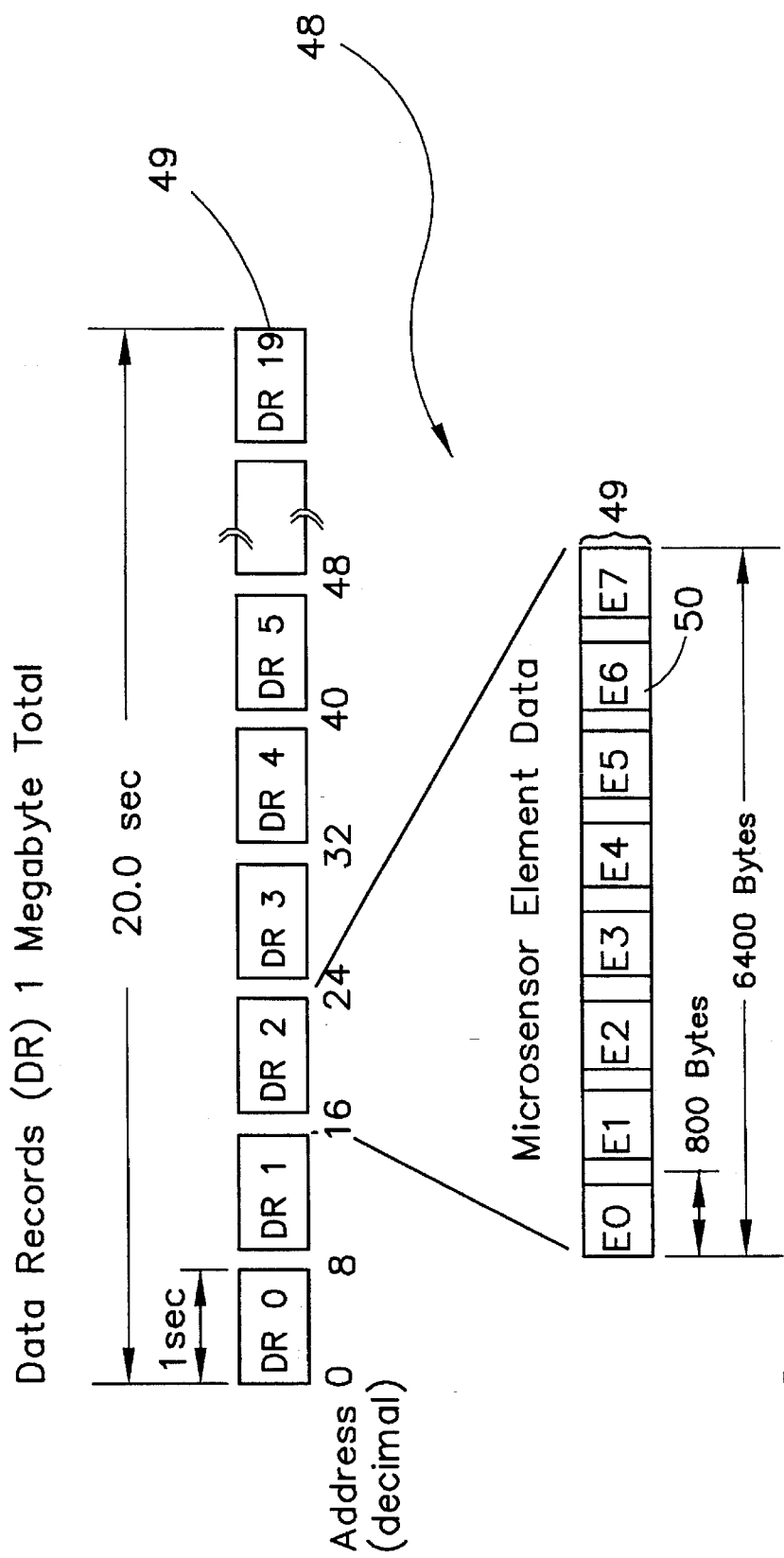
FIG. 8 shows the memory recording format.

FIG. 8 illustrates the fastener 10 data recording format 48. DASM analog arrays 48 are shown organized into 20 data record (DR) segments 49 for a total data base capacity of one megabyte. Each data record 49 of microsensor element data is partitioned into eight sub record segments 50 and contain analog information for each corrosion micro electrode array 17 element (i.e., corrosion product). The eight sub record segments 50, having sample and hold elements 68 as shown in FIG. 8, each contain 800 bytes (a word of an eight bit binary equivalent) of corrosion data or a total of 6400 bytes per data record. Elements 68 make up DASM array 41 which is an ISD 1016 nonvolatile analog memory chip produced by Information Storage Devices Inc. at 2841 Junction Avenue in San Jose, Calif. Memory 40 is described in an article entitled "Nonvolatile Analog Memory Chip" by Frank Goodenough in *Electronic Design* of Jan. 31, 1991. Fastener 10 electronics 36 store a single DR of corrosion information after each power up sequence at programmable time intervals from one day to one week duration. The total memory storage capacity of fastener 10 system goes up to 20 weeks or 5 months before a data debriefing must occur. If fastener 10 system is left in the aircraft structure longer than 5 months, fastener 10 memory 28 will wrap around to the beginning of memory(address 0) and overwrite the existing data record.

Electrochemical micro sensors 72–76 of array 17 detect reactions occurring at the sensor (electrode) surface. Often, sensing surface 25 is metallic, although it could also be glass, ceramic, a polymeric membrane or polymer layer covering a metal, or other chemical coating on a metal. Micro sensors 71–76 are typically immersed in the environment to be tested, usually water, or placed in an environment which has appreciable humidity. The chemical compounds or ions to be detected are dissolved in the water in contact with the sensor 17 surface. The sensing reaction usually involves the addition or removal of an electron from the compound of interest, although absorption of the compound on (or into) the sensor surface (layer) can also be detected. Often, a potential is applied to an electrode (71–76) in order to induce the sensing reactions to occur, or to proceed more rapidly. The electrochemical reactions result in a passage of charge across the boundary (also called the electrochemical interface) between the electrode surface and the solution, and this current flow can be detected using external circuitry. The relationship between the potentials applied to the electrode and the current flow can be used for detection of corrosion products and material loss. This method of analysis is commonly termed voltammetry.

Fastener 10 corrosion micro sensor array 17 layout is shown in FIG. 9. The sensing electrodes 71–76 are arranged at the ends of the "spokes" in the inner circle. There are six micro electrodes (that can all be different materials) per array, each of which is a disc 50 μm in diameter. Electrical contact to the sensors is made through the contact pads at the top.

Micro sensor elements 71–76 are chosen to be specific toward detrimental anions, pH, and corrosion products. The elements are designed for ion selective quantitative measurements of ions present in the electrolyte. For example, element 73 evaluates the pH factor; element 72 detects the presence of sulfide anion ($S^{-2}$); element 71 detects chloride anion ($Cl^-$); element 74 senses for the presence of copper, lead, or aluminum ions; finally, elements 75 and 76 are fabricated from structural materials of interest (e.g., 2024 or 7075 aluminum), for which corrosion parameters are determined. In addition to the sensing electrodes, reference electrode 77 is essential to make corrosion measurements. Reference electrode 77 is a concentric ring around the individual sensing elements. Elements 71–77 are situated on ceramic substrate 25. Elements 74, 75 and 76, for example, have sacrificial metals, wherein each metal selected is the same as that for which corrosion is measured. Each metal is situated at the tip of the respective sensor element. The corrosion within the sensor is parallel to the actual corrosion of the joint or structure being measured. The similarity is that both corrosions have the same electrolyte. The moisture or gas that is in the environment (such as a mere humidity of 60 percent or more of the air or atmosphere in the environment of structure 20) of fastener 10, in a very small part, seeps through the capillary tubes 27, to the sacrificial metals of elements 74–76 in environmental chamber 26 and a corrosion is initiated as shown in FIGS. 3a and 3b wherein there is a transport of ions 78 from cathode 56 to anode 54. The resulting electro-chemical effect results in voltage potential producing a very small current (i.e., nano ampere range) on the respective sensor element relative to reference element 77. Elements 71–76 are in very close proximity to, but are physically separate from, reference element 77. The outputs of sensor array 17 are multiplexed at device 34 so that each output is amplified to a discernible and quantifiable signal by amplifiers 35 and 42 for storage in DASM 41. The amount of corrosion in chamber 26, measured by fastener 10 for a given metal on the sensor element, is indicative of the amount of corrosion of that metal in structure 20 in FIG. 2.

We claim:

1. A smart corrosion sensing fastener comprising:

a fastening means for attaching one item to another item, each item being of a structure;

corrosion sensing means, situated in said fastening means, for simultaneously sensing in-situ a plurality of corrosive effects of ambient environment upon at least one item of structure external of said fastening means, and outputting signals indicative of the corrosive effects; and electronics means, situated in said fastening means and connected to said corrosion sensing means, for processing the signals from said corrosion sensing means, storing the signals for retrieval, and monitoring the signals.

2. The sensing fastener of claim 1 wherein said corrosion sensing means comprises:

a substrate;

a reference electrode formed on said substrate;

at least one sensing electrode, formed on said substrate, having a sacrificial material formed thereon and proximate to said reference electrode, the sacrificial material being the same as a monitored material whose corrosion is to be measured in the ambient environment; and wherein:

if an electrolytic substance from the ambient environment about said fastening means comes in contact with the sacrificial material on said electrode, a corrosion process begins resulting in an electrochemical effect that causes an amount of current to flow between said sensing electrode and reference electrode; and the amount of current is indicative of an amount of corrosion on the sacrificial material, which in turn is indicative of an amount of corrosion on the monitored material.

3. The sensing fastener of claim 2 wherein said electronics means comprises:

an amplifier having an input connected to said sensing electrode and reference electrode, and having an output;

a storage means, having an input connected to said amplifier and having an output, for storing output signals indicative of the amount of corrosion on the monitored material over time;

an interface means, having an input connected to the output of said storage means and having an output, for making available externally of said fastening means the output signals indicative of the amount of corrosion.

4. The sensing fastener of claim 3 wherein said electronics means further comprises a battery power supply.

5. The sensing fastener of claim 4 wherein said fastening means has a removable plug for removing said electronics means from said fastening means.

6. The sensing fastener of claim 5 wherein said fastening means comprises a capillary tube for conveying the electrolytic substance from the ambient environment to said sensing electrode for in-situ corrosion detection.

7. The sensing fastener of claim 6 wherein said storage means performs direct analog storage.

8. A smart fastener comprising:

a bolt having first and second ends and having an opening at the first end;

an internal cavity situated in said bolt proximate to the opening;

at least one corrosion sensor situated in said internal cavity;

at least one conveyance means, connected to said at least one corrosion sensor, for conveying matter to be sensed from an environment external of said bolt; and an electronics module situated in said internal cavity and connected to said corrosion sensing element.

9. The smart fastener of claim 8 further comprising:

a plug, situated in the opening at the first end of said bolt, for enclosing said corrosion sensor in said internal cavity; and a nut at the second end of said bolt.

10. The smart fastener of claim 9 wherein said bolt has at least one capillary tube having a first end proximate to said corrosion sensor and a second end proximate to an environment external to said bolt.

11. The smart fastener of claim 10 wherein said corrosion sensor receives a liquid or gas, via the capillary tube, from the environment and indicates a rate of corrosion for a given material in the environment having the liquid or gas.

12. The smart fastener of claim 11 wherein said electronics module comprises:

a storage device for storing signals indicative of the rate of corrosion; and a power supply connected to said storage device.

13. The smart fastener of claim 12 wherein said storage device is a direct analog storage device.

14. The smart fastener of claim 13 wherein said storage device indicates the date of sensed and stored signals indicative of the rate of corrosion of in-situ measurement.

15. A corrosion detecting fastener comprising:

a fastener for fastening two or more items of structure;

a corrosion sensing module situated within said fastener for sensing corrosion of the two or more items of structure; and an electronics module situated within said fastener and connected to said corrosion sensing module, for processing, monitoring and storing signals from said corrosion sensing module.

16. The corrosion detecting fastener of claim 15 wherein said corrosion sensing module comprises:

a plurality of sensing electrodes; and a reference electrode proximate to said plurality of sensing electrodes.

17. The corrosion detecting fastener of claim 16 wherein said electronics module comprises:

an amplifier connected to said corrosion sensing module;

a storage array connected to said amplifier; and a readout circuit connected to said storage array.

18. The corrosion detecting fastener of claim 17 wherein said storage array is an analog memory.

19. The corrosion detecting fastener of claim 18 wherein said corrosion sensing module further comprises:

a sacrificial material on at least one sensing electrode, the sacrificial material being the same as an attached material around the fastener being monitored, the electrode with the sacrificial material providing a signal to said amplifier indicating corrosion of the sacrificial material; and at least one capillary tube to each sensing electrode of said plurality of sensing electrodes, for conveying ambient atmosphere around said fastener to each sensing electrode.

20. A combined fastener and corrosion sensor comprising:
- a fastener body having a head at a first end and a removable nut at a second end;
- an environmental chamber, situated within said fastener body, said chamber having at least one capillary tube through said fastener body, for channeling electrolyte from about and external to said fastener body to said chamber;
- a corrosion sensing array situated in said environmental chamber, wherein said corrosion sensing array comprises:
  - a reference electrode;
  - at least one sensing electrode proximate to said reference electrode, having a small amount of a first material formed thereon, the first material exposed to electrolyte from the capillary tube and subject to corrosion due to the electrolyte, and if any corrosion occurs, a corrosion signal indicative of corrosion is generated;
- an electronic circuit situated within said fastener body and connected to said corrosion sensing array, wherein said electronic circuit comprises:
  - an analog storage array, connected to said corrosion sensing array for storing corrosion signals from said corrosion sensing array, the corrosion signals indicative of the corrosion of the first material which in turn is indicative of parallel corrosion in a second material attached by said fastener;
  - a clock, connected to said analog storage array, for indicating times of the corrosion signals; and
  - an interface, connected to said analog storage array, for accessing stored corrosion signals and respective times from said analog storage array, the accessing to be performed externally of said fastener.

* * * * *